(12) United States Patent
Hollingsworth

(10) Patent No.: US 6,423,867 B1
(45) Date of Patent: Jul. 23, 2002

(54) PROCESS AND INTERMEDIATE COMPOUNDS FOR THE PREPARATION OF PYRROLIDINES

(75) Inventor: Rawle I. Hollingsworth, Haslett, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 09/946,083

(22) Filed: Sep. 4, 2001

Related U.S. Application Data

(62) Division of application No. 09/630,765, filed on Aug. 2, 2000.

(51) Int. Cl.$^7$ ............................................. C07C 67/08
(52) U.S. Cl. ....................................................... 560/185
(58) Field of Search ........................................... 560/185

(56) References Cited

PUBLICATIONS

Torii et al., Journal of Organic Chemistry, 50(24), 4980–4982, 1985.*
Fleet, G.W.J., et al., Tetrahedron 44(9) 2637–2647 (1988).
Fleet, G.W.J., et al., Tetrahedron 44(9) 2649–2655 (1988).

* cited by examiner

Primary Examiner—Fiona T. Powers
(74) Attorney, Agent, or Firm—Ian C. McLeod

(57) ABSTRACT

Processes for the preparation of pyrrolidones (7 and 8) and pyrrolidines (9 and 10) from tri-O-acetyl-D-erythro-4-pentulosonic acid esters are described. The compounds are aza sugar analogs of D-ribofuranoside and are intermediates to drugs which regulate nucleoside and nucleic acid synthesis.

4 Claims, 2 Drawing Sheets oxidation of peracetate of methyl glycoside of D xylose..furanose
Pulse Sequence: s2pul Tri-O-acetyl-D-erythro-4-pentulosonic acid methyl ester

PROCESS AND INTERMEDIATE COMPOUNDS FOR THE PREPARATION OF PYRROLIDINES

CROSS-REFERENCE TO RELATED APPLICATIONS

This application is a division of application Ser. No. 09/630,765, filed Aug. 2, 2000.

STATEMENT REGARDING FEDERALLY SPONSORED RESEARCH OR DEVELOPMENT

None

BACKGROUND OF THE INVENTION (1) Field of the Invention

The present invention relates to the preparation of pyrrolidines, preferably chiral, from tri-O-acetyl-ketopentulosonic acid methyl esters. In particular the present invention relates to the preparation of 3,4-dihydroxy-5-hydroxymethyl pyrrolidines (1,4-dideoxy-1,4-imino pentitols) which can be substituted or unsubstituted in the N position.

(2) Description of Related Art

Aza-sugar analogs of D-ribofuranosides are important targets for the synthesis of drugs that regulate nucleic acid synthesis. (3R,4R,5R)-3,4-dihydroxy-5-hydroxymethyl-2-pyrrolidone is an important aza-sugar intermediate.

The current routes (Fleet, G. W. J., et al., Tetrahedron 44(9) 2637–2647 (1988); and Fleet, G. W. J., et al., Tetrahedron 44 (9) 2649–2655 (1988)) to 1,4 -dideoxy-1,4-imino-D-ribitol (a pyrrolidine) and its derivatives employ hexose sugars and require the removal of 1 carbon atom (usually by an oxidative process) that is difficult on large scale. One of the methods uses the L-gulono lactone which is a rare sugar and not a regular article of commerce available in significant quantities. There is no relatively simple and economic synthesis available.

OBJECTS

It is therefore an object of the present invention to provide novel intermediates and processes for the preparation of hydroxylated pyrrolidines, preferably chiral, as analogs of D-ribofuranoside. It is further an object of the present invention to provide a process which is relatively easy to perform and economical. These and other objects of the present invention will become increasingly apparent by reference to the following description and the drawings.

SUMMARY OF THE INVENTION

The present invention relates to the preparation of a first intermediate to the pyrrolidines by a process for the preparation of a 2,3,5-tri-O-acetyl-4-ketopentulosonic acid-1-methyl ester which comprises:

(a) reacting a pentose sugar with methanol in the presence of an acid to form a 1-methyl pentose sugar;

(b) reacting the 1-methyl pentose sugar with acetic anhydride in the presence of an amine to form a 1-methyl-2,3,5-tri-O-acetyl pentose sugar; and (c) reacting the 1-methyl-2,3,5-tri-O-acetyl 1-methyl pentose sugar with an oxidizing agent to form the 2,3,5-tri-O-acetyl-4-ketopentulosonic acid-1-methyl ester.

In particular the present invention relates to a process for the preparation of 2,3,5-tri-O-acetyl-D-erythro-4-pentulosonic acid methyl ester which comprises:

(a) reacting D-ribose with an acidic solution of methanol to form 1-methyl D-ribofuranoside;

(b) reacting the 1-methyl D-ribose with acetic anhydride in the presence of pyridine to form 1-methyl-2,3,5 tri-O-acetyl-D-riboside in the reaction mixture; and (d) reacting 1-methyl-2,3,5-tri-O-acetyl-D-riboside with an oxidizing agent to form the 2,3,5-tri-O-acetyl-D-erythro-4-pentulosonic acid methyl ester. The oxidizing agent is preferably chromium trioxide in acetic anhydride. The process is specifically shown in Scheme III.

The present invention also relates to a process for the preparation of a second intermediate to the pyrrolidines which is a process which comprises:

(a) reacting tri-O-acetyl-4-pentulosonic acid methyl ester with hydroxylamine, an amine or an ammonium ion in the presence of pyridine with the hydroxylamine to form an oxime or imine of the formula:

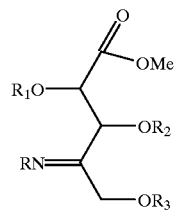

wherein R is selected from the group consisting of acyloxy, alkyloxy, hydroxyl, alkyl, aryl and hydrogen and $R_1$ to $R_3$ are hydrogen or a protecting group;

(b) separating the oxime or imine from the reaction mixture. The reaction is conducted in a non-reactive solvent with an amine base at low temperatures −10° C. to 10° C. and then poured over ice containing an acid to trap the excess amine base or hydroxylamine. In this and the following reactions, R preferably contains 0 to 10 carbon atoms and $R_1$ contains 0 to 10 carbon atoms. R and $R_1$ are generally groups which are non-labile under the reaction conditions.

The present invention also relates to a process for the preparation of a third intermediate to the pyrrolidines which is a process for the preparation of a pyrrolidone lactam of the formula:

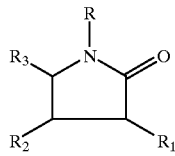

which comprises reducing an oxime or imine of the formula:

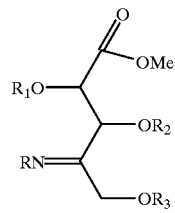

with a source of singlet hydrogen (H) or a hydride to form the pyrrolidone lactam, wherein R is selected from the group consisting of acyloxy, alkyloxy, hydroxyl, alkyl, aryl, and hydrogen, and wherein $R_1$ to $R_3$ are hydrogen or a protecting group and Me is methyl. The reaction is conducted in a non-reactive solvent, preferably methanol, at −10° C. to 30° C.

The present invention also relates to a process for the preparation of a 2,3,5-tri-O-acetyl-1,4-dideoxy-1,4-iminopentitol which comprises:

reacting a pyrrolidone lactam of the formula:

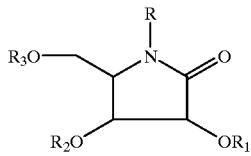

with a source of singlet hydrogen (H) or a hydride to form the pentitol, wherein R is selected from the group consisting of alkyl, aryl and hydrogen and $R_1$ to $R_3$ are hydrogen or a protecting group. The reaction is preferably conducted at −20 to 40° C.

The present invention also relates to a process for the preparation of a lactone which comprises:

(a) reacting in a reaction mixture 2,3,5-tri-O-acetyl-4-pentulosonic acid or ester with a hydride or hydrogen and a catalyst to produce 2,3,5-tri-O-acetyl-pentonic acid or ester in a reaction mixture; and (b) reacting the 2,3,5-tri-O-acetyl-pentonic acid or ester with an acid in water to form a lactone. A preferred lactone is L-lyxono-γ-lactone.

The present invention also relates to a process for the preparation of a 1,4-dideoxy-1,4-imino pentitol which comprises:

(a) reacting tri-O-acetyl -4-pentulosonic acid methyl ester in methanol ammonium acetate and acetic acid in the presence of a hydride reducing agent to form an ammonium compound which spontaneously cyclizes to a lactam;

(b) reacting the lactam with a hydride to form 2,3,5-tri-O-acetyl 1,4-dideoxy-1,4-imino pentitol; and (c) deacylating the tri-O-acetyl-1,4-dideoxy-1,4-iminopentitol to form the 1,4-dideoxy-1,4-iminopentitol.

The present invention also relates to a process for the preparation of 1,4-dideoxy-1,4-aminopentitol which comprises:

(a) reductive cyclization of tri-O-acetyl-4-amino pentonic acid methyl ester with a reducing agent to form 2,3, 5-tri-O-acetyl 1,4-dideoxy-1,4-iminopentitol via an intermediate lactam; and (b) deacylating the 2,3,5-tri-O-acetyl-1,4-dideoxy-1,4-iminopentitol to form 1,4-dideoxy-1,4-imino pentitol.

The present invention also relates to a pentulosonic acid methyl ester which comprises:

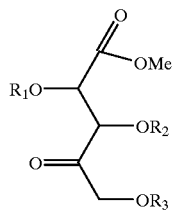

where $R_1$ to $R_3$ is a protecting group or hydrogen and Me is methyl.

The present invention also relates to a pentulosonic acid methyl ester oxime or imine of the formula

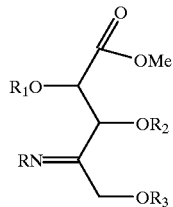

wherein R is selected from the group consisting of acyloxy, alkoxy, hydroxyl, alkyl, aryl and hydrogen, $R_1$ to $R_3$ are protecting groups or hydrogen and Me is methyl.

The present invention also relates to a pyrrolidone of the formula:

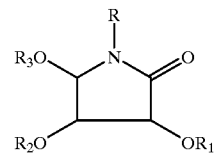

wherein $R_1$ to $R_3$ is a protecting group or hydrogen, and R is selected from the group consisting of acyloxy, alkyloxy, hydroxy, alkyl, aryl and hydrogen.

The present invention also relates to a pyrrolidine of the formula:

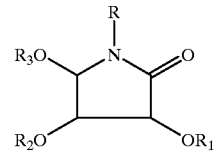

where R is selected from the group consisting of acyloxy, alkyloxy, hydroxy, alkyl, aryl and hydrogen and $R_1$ to $R_3$ is a protecting group.

The specific novel compounds are:

2,3,5-Tri-O-acetyl-D-erythro-4-oximyl pentulosonic acid methyl ester.

2,3,5-Tri-O-acetyl-D-erythro-4-pentulosonic acid methyl ester.

3,4-Dihydroxy-5-hydroxymethyl-2-pyrrolidone.

(3R,4R,5R)-3,4-Dihydroxy-5-hydroxymethyl-2-pyrrolidone.

2,3,5-Tri-O-acetyl-1,4-Dideoxy-1,4-imino-D-ribitol.

2,3,5-Tri-O-acetyl-4-amino-4-deoxy-D-erythro-pentonic acid methyl ester.

N-benzyl (3R,4R,5R)3,4-dihydroxy-5-hydroxymethyl 2-pyrrolidone.

3,4-dihydroxy-5-hydroxymethyl-N-benzyl-2-pyrrolidone.

The present invention further relates to 2,3,5-tri-O-acetyl-L-lyxonic acid methyl ester.

The present invention also relates to lyxono-γ-lactone.

The present invention also relates to L-lyxono-γ-lactone.

Figure 1:
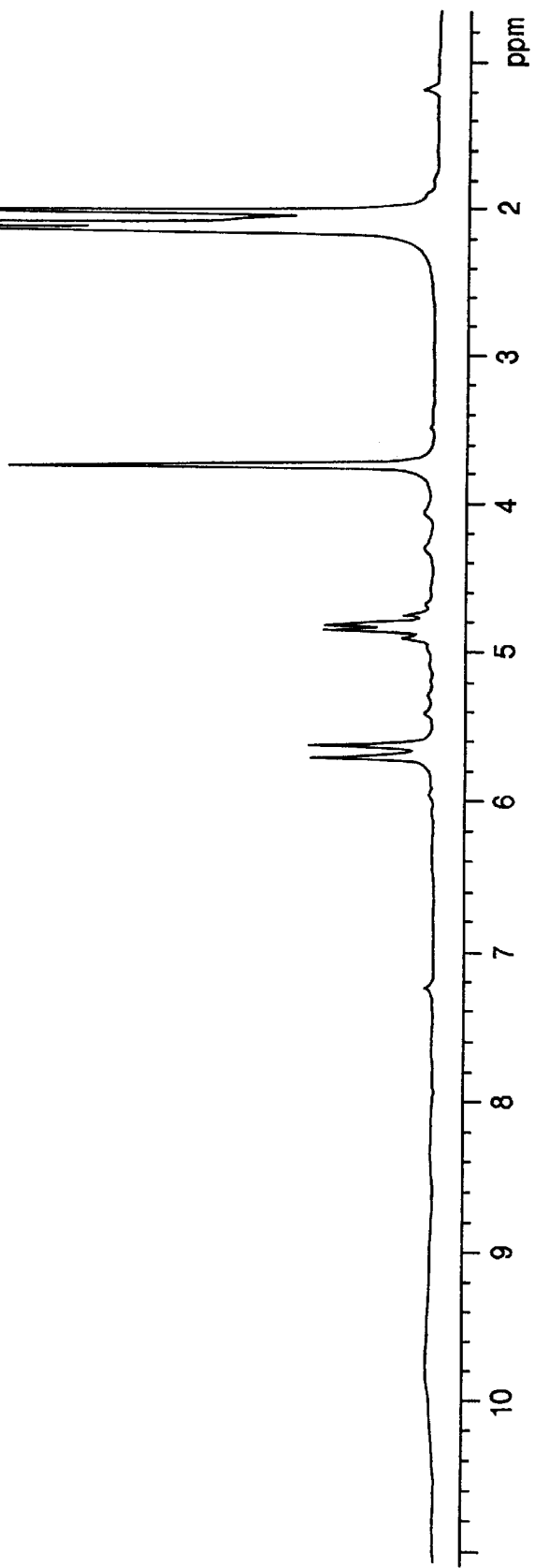
FIG. 1 is a proton NMR spectra for tri-O-acetyl-D-erythro-4-pentulosonic acid methyl ester 6.
Figure 1:

DESCRIPTION OF PREFERRED EMBODIMENTS 1,4-dideoxy-1,4-imino Pentitols from Triacetoxy Keto Pentonic Acids (Tri-O-acetyl Pentulosonic Acid Esters).

The process preferably starts from the pentose D-ribose which is available in ton quantities and has the correct number of carbons and the correct stereochemistries. It is much shorter and more efficient than the other routes. Other pentoses could be used such as L-ribose, D or L arabinose, xylose or lyxose.

1,4-Dideoxy-1,4-imino-D-ribitol is made from tri-O-acetyl D-erythro-4-pentulosonic acid methyl ester or a related molecule by one of several possible methods, the first two of which are:

(1) Reductive amination with an amine or ammonia to form a 4-amino-4-deoxy pentonic acid compound that can then be cyclized to a lactam. Reduction of the lactam with borane or lithium aluminum hydride yields the desired 1,4-dideoxy-1,4-imino-D-ribitol.

(2) Formation of an oxime which can be reduced by one of several possible methods to yield a 4-amino-4-deoxy pentonic acid compound that can then be cyclized to the lactam. Reduction of the lactam with borane or lithium aluminum hydride will yield the desired 1,4-dideoxy-1, 4-imido-D-ribitol.

The tri-O-acetyl D-erythro-4-pentulosonic acid methyl ester, the oxime and the lactam (in these examples (3R,4R, 5R)-3,4-dihydroxy-5-hydroxymethyl-2-pyrrolidone and its N-alkyl derivatives) have not been previously described. Once these compounds can be prepared, the subsequent process step for transformation to the desired 1,4-Dideoxy-1,4-imino-D-ribitol is in the known art.

Tri-O-acetyl D-erythro-4-pentulosonic acid methyl ester, its oxime and (3R,4R,5R)-3,4-dihydroxy-5-hydroxymethyl-2-pyrrolidone and its N-benzyl derivative (formed if benzylamine is used instead of ammonia in the reductive amination) are new compounds.

The pyrrolidines are derived from an appropriately protected ($R_1$ to $R_3$) or unprotected $R_1$ to $R_3$ is hydrogen 2,3,5-trihydroxy 4-ketopentulosonic acid esters 1 by any of several routes as shown in Scheme I.

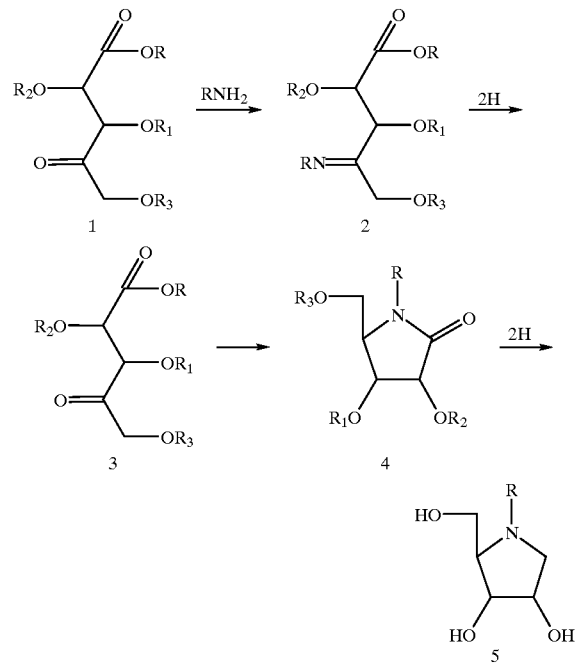

Scheme I wherein R is OH. Steps 2 and 3 combine together, where R is hydrogen or alkyl, aryl, acyloxy, alkoxy then the process follows each of the steps. Generally $R_1$ to $R_3$ is acetyl. Other groups are benzoyl, propanoyl and trifluoroacetyl.

It should be noted that in the present application the compounds can be numbered using the carbohydrate system wherein the carboxyl group is 1 and the compounds are "pyrrolidines. Scheme I uses this carbohydrate system to show the position of the carbons. In the pyrrolidone system the N in the ring is 1 in naming the various compounds. The pyrrolidone system is preferred for purposes of claiming the compounds.

In this scheme the protected trihydroxy 4-ketopentulosonic acid ester 1 is reacted with ammonia or a primary amine or ammonium ion or with hydroxylamine to form an imine (in the former case) or an oxime 2 where R is OH which is then hydrogenated or reduced with a metal or a metal hydride reagent to form an amine 3. The amine spontaneously cyclizes to a lactam 4 which can be reduced with borane or a hydride reagent to the desired pyrrolidine 5.

Starting with the previously unknown compound tri-O-acetyl-D-erythro-4-pentulosonic acid methyl ester (R=methyl, $R_1$ to $R_3$=acetyl in Scheme I) (6), direct syntheses of the tri and di hydroxypyrrolidines (9 and 10 respectively) is obtained with the D-ribo configuration (scheme II). The deoxygenation of the 5-position to form 10 was produced by reduction of the triacetate of the oxime (2) with hydrogen on palladium in acetic acid and thus this combination is not used as a reducing agent. Under these conditions the amino group was also introduced by reduction of the oxime 2. The amine cyclized to form the intermediate amide 8 (lactam) which was reduced to the pyrrolidine 10 with borane or lithium aluminum hydride. Deoxygenation of the 5-position did not occur if the molecule was deactylated first or if an imine was used instead of an oxime for introducing the nitrogen.

Scheme II

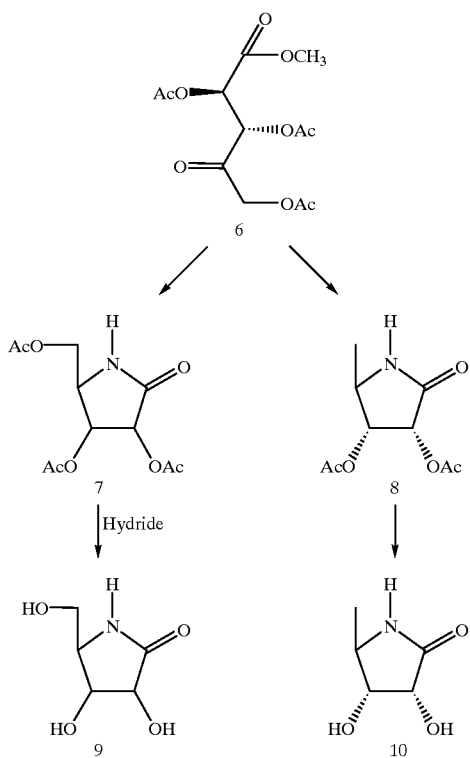

Tri-O-acetyl-D-erythro-4-pentulosonic acid methyl ester (6) was prepared by two routes as outlined in Schemes III and IV.

Scheme III

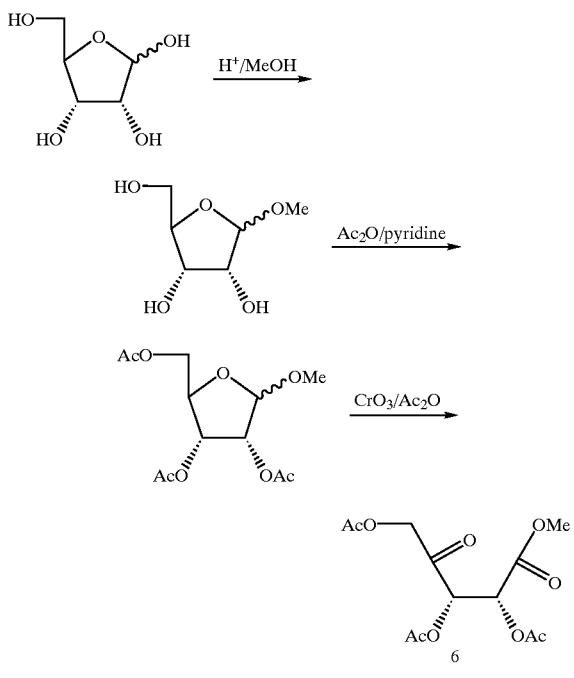

Scheme IV

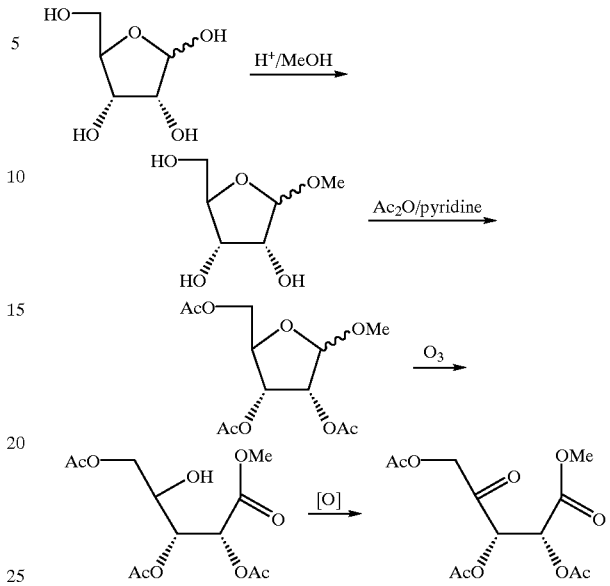

Figure 2:
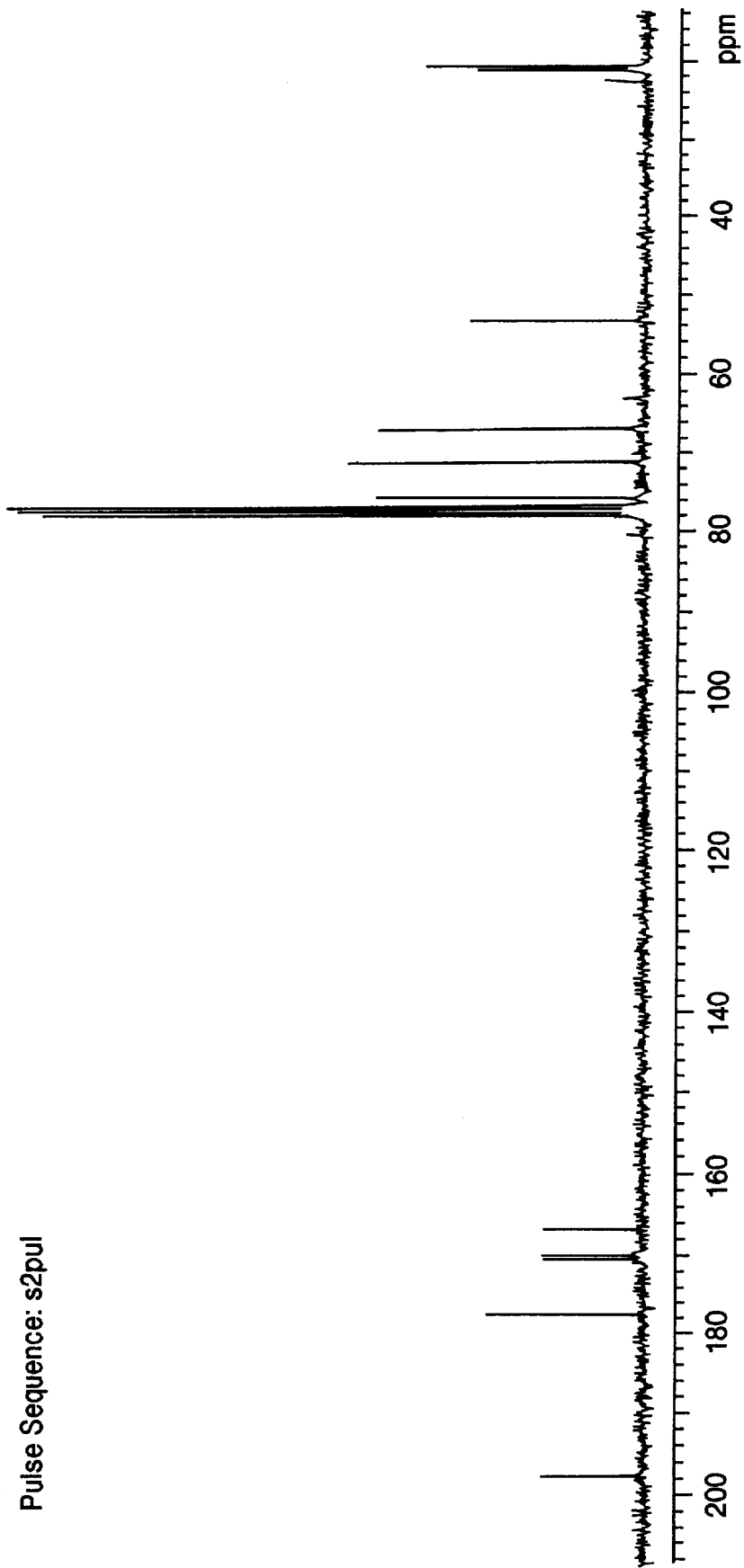
FIG. 2 is a 13C NMR spectra for the compound 6 of FIG. 1.

In the first route (Example 1, Scheme III), D-ribose is converted to a mixture of its α and β furanosides by treatment with methanol in the presence of a catalytic amount of sulfuric acid. The methyl glycosides are peracetylated and then oxidized with chromium trioxide in acetic anhydride (Example 2). This yields the Tri-O-acetyl-D-erythro-4-pentulosonic acid methyl ester (6) in very pure state as evidenced by the proton (FIG. 1) and 13C NMR spectra (FIG. 2).

In the second route (Example 6, Scheme IV) the peracetylated glycosides are oxidized with ozone to give the 2,3,5-triacetyl aldonic acid methyl ester which is then oxidized to the tri-O-acetyl-D-erythro-4-pentulosonic acid methyl ester 6 by treatment with DMSO and acetic anhydride or DMSO and trifluoroacetic anhydride.

The pentulosonic acid methyl ester 6 can be converted to the pyrrolidine nucleus by several routes:

(1) Conversion to the oxime 2 and reduction to the 4-amino-4-deoxy ester 3 with hydrogen Pd/C with concomitant deoxygenation at the 5 position followed by cyclization to form 10 (Scheme II) where R=H and $R_1=R_2$=Ac.

(2) Deacetylation by acid methanolysis, oxime 2 formation, and reduction with Pd/C to form 7 where R=$R_1$=$R_2$=$R_3$= H.

(3) Reductive amination with ammonia and a reductant to form the 4-amino-4-deoxy ester 3 followed by cyclization to form 7 where R=H $R_1$=$R_2$=$R_3$=Ac.

(4) Conversion to the oxime 2, deacetylation with hydrazine, reduction to the 4-amino-4-deoxy ester 3 with hydrogen Pd/C with concomitant deoxygenation at the 5 position followed by cyclization to from 7 where R=$R_1$=$R_2$=$R_3$= H.

(5) Reductive amination with benzylamine and a reductant to form the 4-amino-4-deoxy ester 3 followed by cyclization to form 7 where R=Benzyl and $R_1$=$R_2$=$R_3$=Ac.

(6) Reductive amination with 2,4-dimethoxybenzyiamine and a reductant to form the 4-amino-4-deoxy ester 3 followed by cyclization to form 11 where R=Benzyl and $R_1$=$R_2$=$R_3$=Ac.

Tri-O-acetyl D-erythro-4-pentulosonic acid methyl ester 6 is thus a key intermediate in the synthesis of (3R,4R,5R)-3,4-dihydroxy-5-hydroxymethyl-2-pyrrolidone as a 1,4-dideoxy-1,4-imino-D-ribitol (9). These compounds are valuable intermediates in the synthesis of "aza-sugar" analogs of D-ribofuranose.

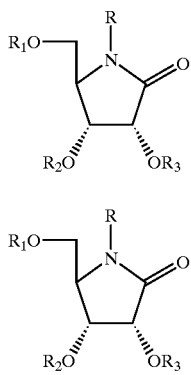

The transformation of tri-O-acetyl D-erythro-4-pentulosonic acid methyl ester 6 and its oxime 2 to 9 via 7 and its per-O-acetate was achieved via various chemical transformations. Typical strategies are:
(1) Reduction of the oxime to an amine and cyclization to the pyrrolidone with expulsion of methanol with reagents such as hydrogen and palladium, hydrogen and platinum, hydrogen and Raney nickel, zinc and acetic acid and sodium cyanoborohydride.
(2) Reductive amination of the ketone function of tri-O-acetyl D-erythro-4-pentulosonic acid methyl ester 6 with ammonia or an amine using reagents such as sodium cyanoborohydride, sodium borohydride or hydrogen and a catalyst followed by cyclization to the pyrrolidone. The pyrrolidone is reduced to the 1,4-dideoxy-1,4-imino-D-ribitol with reagents such as lithium aluminum hydride or borane.

EXAMPLE 1

Preparation of Tri-O-acetyl D-erythro-4-pentulosonic Acid Methyl Ester 6

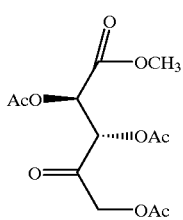

There are two efficient routes to the preparation of tri-O-acetyl D-erythro-4-pentulosonic acid methyl ester 6. The first route is by the oxidation of tri-O-acetyl methyl α,β-ribofuranoside with chromium trioxide in acetic acid/acetic anhydride. The second method is by the oxidation of tri-O-acetyl methyl α,β-ribofuranoside with ozone to produce 2,3,5-tri-O-acetyl D-ribo-pentonic acid methyl ester which is then oxidized with a reagent such as DMSO/TFAA or DMSO/Ac$_2$O.

Tri-O-acetyl Methyl α,β-ribofuranoside

Procedure 1.

D-ribose (100 g) was dissolved in methanol (1000 ml) and conc sulfuric acid (2 ml) added. The mixture was left at room temperature for 24 hours and then the solvent was removed at a bath temperature of less than 30–35° C. Pyridine (400 ml) was added and the mixture cooled in ice to ~5° C. Acetic anhydride (300) was then added over a 20 minute period. The mixture was allowed to come to room temperature and left there for 10 hours after which the solvents were removed by rotary evaporation at a bath temperature of 45–50° C. The syrup was dissolved in ethyl acetate (1000 ml) and washed twice with cold saturated sodium chloride (200 ml) containing ~30 ml of conc HCl. After 1 wash with cold saturated sodium chloride (100 ml), the solution was dried (sodium sulfate) and concentrated to an oil. The crude tri-O-acetyl methyl α,β-D-ribofuranoside that was so produced was used without further purification.

Tri-O-acetyl D-exythro-4-pentulosonic Acid Methyl Ester

The tri-O-acetyl methyl α,β-ribofuranoside prepared from 100 g of D-ribose by procedure 1 above was dissolved in acetic acid (1500 ml) and acetic anhydride (330 ml) added. The mixture was cooled in ice to 0–5° C. and a stream of nitrogen passed over the surface. Chromium trioxide (130 g) was added over a period of 40 minutes and the temperature never allowed to exceed 10° C. The mixture was stirred at this temperature for 1 hour then allowed to reach room temperature over a 30 minute period. It was stirred at room temperature for 5 hours. The solvents were then rapidly removed under vacuum at a temperature not to exceed 50° C. It was then diluted with 2000 ml of ethyl acetate, stirred vigorously for 30 minutes and filtered. The filter cake was washed with a further 500 ml of ethyl acetate. The combined ethyl acetate extracts was washed with 2×300 ml of cold water, dried and the solvent removed to yield the desired product in over 92% yield (>92% pure by NMR spectroscopy). $^1$H NMR in chloroform, 2.0–2.3 (3×3H singlets), 4.8 (dd, 2H, J=12 Hz), 5.61 (s, 1H), 5.71 (s, 1H). $^{13}$C NMR 30–31 ppm (3 signals), 53.2, 66.8, 71.3, 76.0, 166.7, 169.5, 170.5, 197.8.

Preparation of tri-O-acetyl D-erythro-4-pentulosonic Acid Methyl Ester Oxime (2), Where R=H and R$_1$ to R$_3$=Acetyl

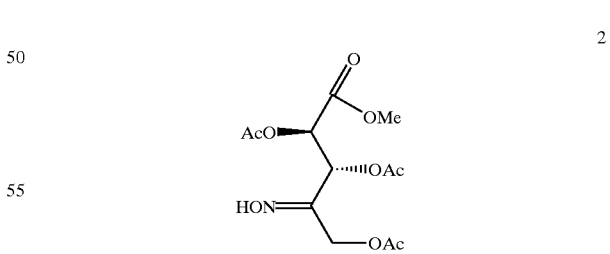

Tri-O-acetyl D-erythro-4-pentulosonic acid methyl ester (5.5 g) was dissolved in pyridine (16 ml) and the solution cooled to 0° C. Hydroxyamine hydrochloride (2 g, 29 mmol) was added and the mixture was kept at 0° C. for a further 15 minutes and then at room temperature for 2 hours. It was poured into ice containing 18 ml of concentrated HCl (sufficient to neutralize the pyridine) and extracted with 3 times with 60 mol of chloroform. The combined chloroform extracts were washed once with 15 ml of cold saturated sodium chloride, dried (anhydrous sodium sulfate) and concentrated to yield a colorless syrup which slowly formed white crystals. Yield—5.7 g (97%). 13 C NMR-(d-chloroform) 21.0, 53.5, 57.8, 62.0, 68.3, 70.8, 72.0, 151.6, 168.0, 170.1, 171.1, 172.0.

EXAMPLE 3

N-benzyl (3R,4R,5R)-3,4-dihydroxy-5-hydroxymethyl-2-pyrrolidone

Tri-O-acetyl D-erythro-4-pentulosonic acid methyl ester 6 (15.2 g) was dissolved in methanol (85 ml) and acetic acid (3.1 g) and benzylamine (5.4 g) added. Sodium cyanoborohydride (3.11g) was then added and the mixture kept at room temperature for 24 hours to reduce the imine to an amine 3. Sodium bicarbonate (6 g) and water 20 ml was added and the mixture heated for 4 hours at 70° C. to effect cyclization to the lactam 7. The mixture was concentrated to a syrup and partitioned between ethyl acetate (300 ml) and cold saturated sodium chloride (100 ml). The ethyl acetate layer was recovered, dried (sodium sulfate) and concentrated to a syrup. The syrup was dissolved in methanol (200 ml) to which was added potassium carbonate 20 g and water 2 ml. The resulting mixture was stirred at room temperature for 14 hours, filtered, the filtrate concentrated and the resulting syrup dissolved in methanol (400 ml). Concentrated HCl (4.1 ml) was added. A white solid was formed. This was removed by filtration and the filtrate concentrated to dryness. Methanol was added again and the solution again concentrated. This was repeated one more time to give the crude N-benzyl pyrrolidone which can be converted to the pyrrolidine to reduction.

EXAMPLE 4

(3R,4R,5R)-3,4-dihydroxy-5-hydroxymethyl-2-pyrrolidone

Procedure 1

Tri-O-acetyl D-erythro-4-pentulosonic acid methyl ester 6 (15.2 g) was dissolved in methanol (100 ml) and ammonium acetate (3.0 g) and acetic acid (0.2 ml) added. Sodium cyanoborohydride (3.1 g) was then added and the mixture kept at room temperature for 24 hours to reduce the ammoniated compound to an amino group which are rearranged to the tri-acetylated product 4. The triacetylated product was deacetylated with potassium carbonate-methanol to form the pyrrolidone.

Procedure 2

Tri-O-acetyl D-erythro-4-pentulosonic acid methyl ester oxime wherein R=H and $R_1$ to $R_3$=acetyl (3.1 g) was dissolved in methanol (40 ml) and Raney nickel (0.5 g) added. The mixture was hydrogenated at 2 atmospheres for 6 hours, filtered and concentrated to give the crude triacetylated product. The product was deactylated with potassium carbonate-methanol to form the pyrrolidone.

Procedure 3

The oxime derivative formed above was treated with 4 equivalents of hydrazine in methanol for 4 hours and then hydrogenated with 10% Pd/C in ethanol containing 10% acetic acid at 50 psi and room temperature for 5 hours. The product was deacetylated with potassium carbonate—methanol to form the pyrrolidone.

In these procedures, the intermediate steps of 3 and 4 Scheme I are by-passed to produce the tri-O-acetylated intermediate pyrrolidone and the intermediate tri-O-acetylate pyrrolidone is then deacylated and reduced to the pyrrolidine (pentitol 5 in Scheme I).

EXAMPLE 5

The following is an additional procedure (Scheme V) for using the tri-O-acetyl-D-erythro-4-pentulosonic acid methyl ester 6 to form the pyrrolidine.

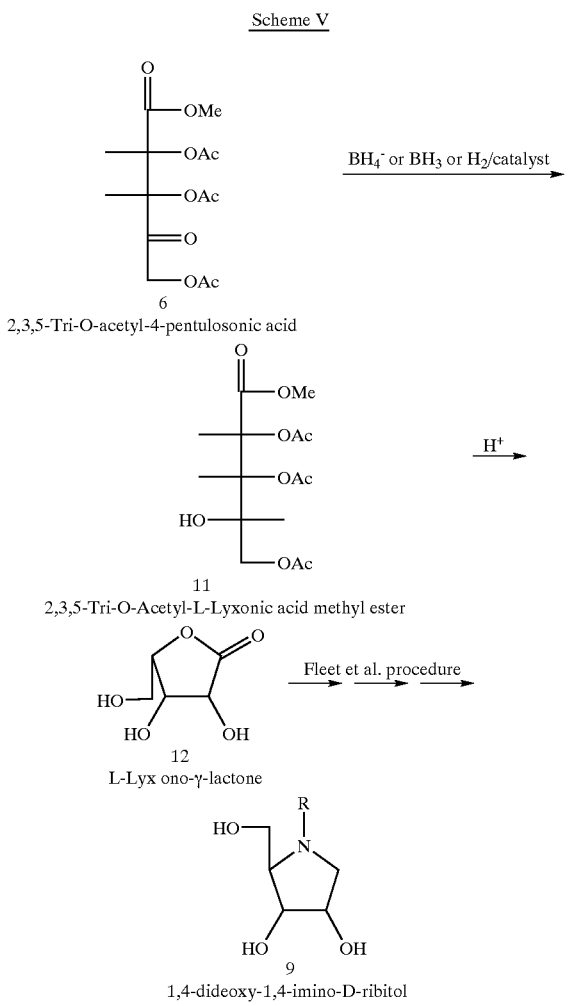

In a typical step, the 4-pentulosonic acid (30 g) is dissolved in 150 ml of methanol and 0.5 molar equivalents of sodium borohydride is added after the solution is cooled to 0° C. The mixture is maintained at 0–50 for 2 hours and then 4 equivalents of acetic acid are added to decompose the borohydride. The methanol is removed by rotary evaporation. 200 ml of methanol is added and removed and this process of adding method and removing repeated four times to remove all borate esters. The product 11 is refluxed in 300 ml of methanol containing 1% HCl for 3 hours, to effect deacylation and concentrated to effect lactonization. The crude L-lyxono-γ-lactone 12 so obtained is converted to the iminopentitol 9 using procedures such as that described by Fleet et al, cited previously.

EXAMPLE 6

Methyl tri-O-acetyl-α,β,D-ribofuranoside (2 g) was dissolved in ethyl acetate (30 ml) and the solution was cooled to 0–10° C. Ozone was passed through for 2 hours at the rate of 20 mM per hour. The ethyl acetate was then removed and the product dissolved in dimethyl pentoxide (30 ml) and acetic anhydride (2 ml) added. The mixture was left at room temperature for 24 hours. The keto ester was isolated by concentration, and partitioning between water/ethyl acetate. The product was recovered from the ethyl acetate layer.

It is intended that the foregoing description be only illustrative of the present invention and that the present invention be limited only by the hereinafter appended claims.

I claim:

1. A process for the preparation of a 2,3,5-tri-O-acetyl-4-ketopentulosonic acid methyl ester which comprises:
    (a) reacting a pentose sugar with methanol in the presence of an acid to form a 1-methyl pentose sugar;
    (b) reacting the 1-methyl pentose sugar with acetic anhydride in the presence of an amine to form a 1-methyl-2,3,5-tri-O-acetyl pentose sugar; and
    (c) reacting the 1-methyl-2,3,5-tri-O-acetyl pentose sugar with an oxidizing agent to form the 2,3,5-tri-O-acetyl-4-pentulosonic acid methyl ester.

2. A process for the preparation of 2,3,5-tri-O-acetyl-D-erythro-4-pentulosonic acid methyl ester which comprises:
    (a) reacting D-ribose with an acidic solution of methanol to form 1-methyl D-ribofuranoside;
    (b) reacting the 1-methyl D-ribose with acetic anhydride in the presence of pyridine to form 1-methyl-2,3,5 tri-O-acetyl-D-riboside in the reaction mixture; and
    (d) reacting 1-methyl-2,3,5-tri-O-acetyl-D-riboside with an oxidizing agent to form the 2,3,5-tri-O-acetyl-D-erythro-4-pentulosonic acid methyl ester.

3. The process of claim 2 wherein in step (d) the oxidizing agent is an oxygen providing metal compound in acetic anhydride.

4. The process of claim 2 wherein in step (d) the oxidizing agent are ozone and dimethyl sulfoxide and an acid anhydride or chloride.

* * * * *